US005843671A

United States Patent [19]
Zakian et al.

[11] Patent Number: 5,843,671
[45] Date of Patent: Dec. 1, 1998

[54] METHODS FOR MEASURING TRINUCLEOTIDE REPEAT EXPANSION IN *SACCHAROMYCES CEREVISIAE*

[75] Inventors: Virginia Zakian; Catherine Freudenreich, both of Princeton, N.J.

[73] Assignee: Princeton University, Princeton, N.J.

[21] Appl. No.: 50,108

[22] Filed: Mar. 30, 1998

Related U.S. Application Data

[60] Provisional application No. 60/042,561 Apr. 1, 1997.
[51] Int. Cl.$^6$ ....................................................... C12Q 1/68
[52] U.S. Cl. .................................................................. 435/6
[58] Field of Search ........................ 435/6, 172.3, 254.21

[56] References Cited

PUBLICATIONS

Ashley and Warren "Trinucleotide Repeat Expansion and Human Disease", (1995) *Annu. Rev. Genet.*, 29:703–728.
Bingham et al., "Stability of an expanded trinucleotide repeat in the androgen receptor gene in transgenic mice", (1995) *Nature Genet.*, 9:191–196.
Brook et al., "Molecular Basis of Myotonic Dystrophy: Expansion of a Trinucleotide (CTG) Repeat at the 3' End of a Transcript Encoding a Protein Kinase Family Member", (1992) *Cell*, 68:799–808.
Caskey et al., Triplet Repeat Mutations in Human Disease, (1992) *Science*, 256:784–789.
Flynn et al., "Identification of the FRAXE fragile site in two families ascertained for X linked mental retardation", (1993) *J. Med. Genet.*, 30:97–100.
Fu et al., "An Unstable Triplet Repeat in a Gene Related to Myotonic Muscular Dystrophy", (1992) *Science*, 255: 1256–1258.
Fu et al., "Decreased Expression of Myotonin–Protein Kinase Messenger RNA and Protein in Adult Form of Myotonic Dystrophy", (1993) *Science*, 260:235–238.
Gerber et al., "Transcriptional Activation Modulated by Homopolymeric Glutamine and Proline Stretches", (1994) *Science*, 263:808–811.
Group THDCR, "A Novel Gene Containing a Trinucleotide Repeat That Is Expanded and Unstable on Huntington's Disease Chromosomes", (1993) *Cell*, 72:971–983.
Harper et al., "Anticipation in Myotonic Dystrophy: New Light on an Old Problem", (1992) *Am. J. Hum. Genet.*, 51:10–16.
Jacobsen et al., "An (11;12) Translocation in Four Generations with Chromosome 11 Abnormalities in the Offspring", (1973) *Hum. Hered.*, 23:568–585.
Jones et al., "Physical linkage of the fragile site FRA11B and a Jacobsen syndrome chromosome deletion breakpoint in 11q23.3", (1994) *Hum. Mol. Genet.*, 3:2123–2130.
Kawaguchi et al., "CAG expansions in a novel gene for Machado–Joseph disease at chromosome 14q32.1", (1994) *Nature Genet.*, 8:221–228.
Kunst and Warren, "Cryptic and Polar Variation of the Fragile X Repeat Could Result in Predisposing Normal Alleles", (1994) *Cell*, 77:853–861.

La Spada et al., "Trinucleotide Repeat Expansion in Neurological Disease", (1994) *Ann. Neurol.*, 36:814–822.
Malter et. al., "Characterization of the full fragile X syndrome mutation in fetal gametes", (1997) *Nature Genetics*, 15:165.
Nagafuchi et al., "Dentatorubral and pallidoluysian atrophy expansion of an unstable CAG trinucleotide on chromosome 12p", (1994) *Nature Genet.*, 6:14–18.
Orr et al., "Expansion of an unstable trinucleotide CAG repeat in spinocerebellar ataxia type 1", (1993) *Nature Genet.*, 4:221–226.
Reyniers et al., "The full mutation in the FMR–1 gene of male fragile X patients is absent in their sperm", (1993) *Nature Genet.*, 4:143–146.
Richards and Sutherland, "Dynamic Mutations: A New Class of Mutations Causing Human Disease", (1992) *Cell*, 70:709–712.
Richards et al., "Fragile X syndrome unstable element, p(CCG)n, and other simple tandem repeat sequences are binding sites for specific nuclear proteins", (1993) *Hum. Mol. Genet.*, 2:1429–1435.
Richards and Sutherland, "Simple repeat DNA is not replicated simply", (1994) *Nature Genet.*, 6:114–116.
Richards and Sutherland, "Simple tandem DNA repeats and human genetic disease", (1995) *Proc. Natl. Acad. Sci.*, 92:3636–3641.
Schulz and Zakian, "The Saccharomyces PIF1 DNA Helicase Inhibits Telomere Elongation and De Novo Telomere Formation", (1994) *Cell*, 76:145–155.
Sugawara and Haber, "Characterization of Double–Strand Break–Induced Recombination:Homology Requirements and Single–Stranded DNA Formation", (1992) *Mol. and Cell. Biol.*, 12:563–575.
Verkerk et al., "Identification of a Gene (FMR–1) Containing a CGG Repeat Coincident with a Breakpoint Cluster Region Exhibiting Length Variation in Fragile X Syndrome", (1991) *Cell*, 65:905–914.
Wang et al., "Preferential Nucleosome Assembly at DNA Triplet Repeats from the Myotonic Dystrophy Gene", (1994) *Science*, 265:669–671.
Weber, "Informativeness of Human (dC–dA)$^n$ (dG–dT)$^n$ Polymorphisms", (1990) *Genomics*, 7:524–530.
C. Jones, et al., Association of a chromosome deletion syndrome with a fragile site within the proto–oncogene CBL2, (1995) *Nature*, 376:145–149.
Maurer et al., *Mol. Cell. Biol.*, vol. 16, Dec. 1996, pp. 6617–6622.

*Primary Examiner*—James Ketter
*Attorney, Agent, or Firm*—Law Offices of Jane Massey Licata

[57] ABSTRACT

Assays for measuring fragility or breakage of chromosomes at trinucleotide repeats in *Saccharomyces cerevisiae* are provided. These assays can also be used to measure trinucleotide repeat expansion and to screen drugs, proteins and cellular conditions which increase or decrease this expansion.

4 Claims, 3 Drawing Sheets ial No. 60/042,561, filed 1 Apr. 1997.

METHODS FOR MEASURING TRINUCLEOTIDE REPEAT EXPANSION IN *SACCHAROMYCES CEREVISIAE*

This application claims the benefit of U.S. Provisional Application No. 60/042,561, filed 1 Apr. 1997.

INTRODUCTION

This invention was made in the course of research sponsored by the National Institutes of Health. The U.S. Government may have certain rights in this invention.

BACKGROUND OF THE INVENTION

In addition to Mendelian inherited traits (genes) and associated controlling elements, the human genome consists of long stretches of deoxyribonucleic acid (DNA), with no discernible function. A large subset of these DNA stretches are characterized as repetitive nucleotide sequences. Some of these repeated sequences are genes, such as ribosomal RNA genes, which have arisen through duplication events throughout evolution. However, the majority of these sequences are simple, tandemly repeated di-, tri-, tetra-, and pentanucleotide repeating units (STRs) which tend to be widely dispersed throughout the genome. The purpose of these types of variable number tandem repeats (VNTRs) is not known. However, sequence-specific DNA binding proteins have been shown to bind to di- and trinucleotide repeats and at least one of the repeats has been reported to act as a preferential site of nucleosome assembly in vitro (Richards et al. (1993) *Hum. Mol. Genet.*, 2:1429–1435; Wang et al. (1994) *Science*, 265: 669–671).

In general, STR repeat sequences are highly polymorphic in copy number throughout the human population. Accordingly, one characteristic of STRs is a variability in the number of repeats (Weber (1990) *Genomics*, 7:524–530). The length of imperfection is directly tied to an increase in the instability of the DNA strand. Most changes are limited to the addition or deletion of a small number of repeat units, however some trinucleotide repeats undergo more dramatic expansions, increasing 10- to 100-fold in size (Richards and Sutherland (1992) *Cell*, 70:709–712; Richards and Sutherland (1995) *Proc. Natl. Acad. Sci.*, 92:3636–3641). These dramatic expansions occur during passage of the genetic material from one generation to the next. In addition, in comparison to a conventional mutation event, as the trinucleotide repeat increases in size, it has a greater risk of further expansion, thus it is a dynamic mutation. It has been shown that the risk of expansion is a function of the number of perfect repeating units. It is not known whether the dynamic mutation of a DNA repeat sequence from a harmless copy number polymorphism to a disease-causing length typically involves small, multiple changes or a single event (Richards and Sutherland (1994) *Nature Genet.*, 6:114–116). Trinucleotide repeats in the normal range are small, stable polymorphisms with a relatively low mutation rate. It is believed that trinucleotide repeat expansion is due to slippage occurring during lagging strand synthesis of DNA replication (Richards and Sutherland (1994) *Nature Genet.*, 6:114–116; Kunst and Warren (1994) *Cell*, 77:853–861).

Approximately eleven human loci, responsible for nine genetic diseases have been identified in which a normally polymorphic trinucleotide repeat undergoes a mutational change whereby the repeat length expands, often quite substantially (Ashley and Warren (1995) *Annu. Rev. Genet.*, 29:703–728). These disease-causing repeat expansions have been grouped into two families; CCG/CGG and CTG/CAG complementary sequences. The designations depend upon the first base of a repeat tract (e.g. GCC is equivalent to a CCG or a CGG repeat) or upon which strand is coding, if the mutation is in context of a gene. The CCG/CGG repeats usually involve noncoding triplets. When expanded, these loci are often associated with chromosome fragile sites and the amount of expansion is usually quite substantial. In contrast, the CTG/CAG repeats are in most instances associated with coding regions, and when expanded (usually not as dramatically as the CCG/CGG repeats) are often associated with neurodegenerative diseases. However, a CTG/CAG repeat expansion in the 3' UTR of the DM gene has been reported which can expand from the normal length of about 30 repeats up to 1000 or more repeats, causing the disease myotonic dystrophy (Fu et al. (1992) *Science*, 255:1256–1258).

There are at least five instances of chromosome fragility associated with expansion of a CCG/CGG sequence. Three of these expansions are known to be associated with human disease. Fragile X syndrome (FRAXA), Fragile XE mental retardation (FRAXE), and Jacobsen syndrome (FRA11B) all involve CCG/CGG expansions up to a thousand-fold (Verkerk et al. (1991) *Cell*, 65:905–914; Flynn et al. (1993) *J. Med. Genet.*, 30:97–100; Jacobsen et al. (1973) *Hum. Hered.*, 23: 568–585). FRAXA and FRAXE are correlated with abnormal methylation at CpG islands upstream of these loci and a loss of function of the downstream gene. Aberrant methylation of CpG islands usually affects transcription of a downstream gene. The expanded trinucleotide repeat fragile site is also cytogenetically visible by determination of chromosome breakage, e.g., Jacobsen syndrome, (Jones et al. (1994) *Hum. Mol. Genet.*, 3:2123–2130). These fragile site mutations cause a variety of mental retardation phenotypes ranging from mild to severe. Fragile X syndrome, the most prevalent of these types of diseases and the most common form of inherited mental retardation, is X-linked and thus more severe in the male carrier (Reyniers et al. (1993) *Nature Genet.*, 4:143–146). It is not clear when the expansion mutation occurs, but recent evidence suggests that the full mutation is present in the egg (meiotic division) or occurs very early in development immediately after the fertilized egg starts dividing (mitotic division) (Malter et. al. (1997) *Nature Genetics*, 15:165).

Disease phenotypes correlated with CTG/CAG trinucleotide repeat expansions are primarily neurodegenerative in nature. Disorders involving CTG/CAG expansions in the coding regions of genes include Huntington's disease (HD), Kennedy's disease (spinal and bulbar muscular atrophy-SBMA), spinocerebellar ataxia, type 1 (SCA1), and Machado-Joseph disease (spinocerebellar ataxia, type 3) (Group THDCR (1993) *Cell*, 72:971–983; Bingham et al. (1995) *Nature Genet.*, 9:191–196; Orr et al. (1993) *Nature Genet.*, 4:221–226; Kawaguchi et al. (1994) *Nature Genet.*, 8:221–228). CAG/CTG expansions (and in some cases contractions) causing disease states have also been implicated in the non-coding, 3' untranslated region of at least one gene (DM protein kinase) (Fu et al. (1992) *Science*, 255: 1256–1258; Fu et al. (1993) *Science*, 260:235–238). The aberrant processing of this gene is involved in autosomal myotonic dystrophy, the most common form of adult muscular dystrophy (Brook et al. (1992) *Cell*, 68:799–808).

Unlike the CCG/CGG expansions, the CAG/CTG expansions usually affect the protein directly (myotonic dystrophy being the exception) (La Spada et al. (1994) *Ann. Neurol.*, 36:814–822) and manifest as a gain or alteration in function, not a loss of function. These disorders are essentially confined to the nervous system and are caused by modest expansions of CAG/CTG in the DNA sequence that are translated into large polyglutamine tracts in the protein (Nagafuchi et al. (1994) *Nature Genet.*, 6:14–18). These polyglutamine additions are believed to alter some function of the protein (polyglutamine tracts are often found in transactivation factors), which appears to be particularly toxic to neurons (Gerber et al. (1994) *Science*, 263:808–811). In contrast to the CCG/CGG expansions, the CAG/CTG expansions (except those associated with the DM locus) usually do not exceed three times the normal repeat length.

All trinucleotide repeat disorders show instability in transmission of the expanded repeat from parents to offspring. In addition, larger repeat expansions are often associated with more severe disease phenotype (Caskey at al. (1992) *Science*, 256:784–789). The increasing repeat length with successive generations is associated with the phenomenon of genetic anticipation characteristic of trinucleotide repeat diseases (Harper et al. (1992) *Am. J. Hum. Genet.*, 51:10–16). This phenomenon of genetic anticipation may also be applicable to other disorders of complex inheritance, such as psychiatric diseases like schizophrenia and bipolar affective disorder (Ashley and Warren et al. (1995) *Ann. Rev. Genet.*, 29:703–728; Rubinstein et al. (1996) *Am. J. Hum. Genet.*, 67:495–498). Increased repeat length also correlates with other clinical features such as early onset (SCA 1) or early death (HD) (La Spada et al. (1994) *Ann. Neurol.*, 36:814–822).

Trinucleotide repeats are typically identified by polymerase chain reaction (PCR), Southern hybridization and in situ hybridization. However, as yet, there are no known animal model equivalents of the human dynamic mutations of these trinucleotide repeats which can be used to measure the properties of repeat expansion. Mouse homologues of each of these altered genes are known for a shorter repeat length and a lower polymorphism. This apparent lack of unstable repeats in the mouse genome and the greater stability of repeats at homologous loci suggests that the process of dynamic mutation may be restricted to the human genome. It has been suggested that if the interspecies intracellular metabolism is similar, the late onset dynamic mutation diseases of humans may not have time to manifest in species other than humans (Sutherland and Richards (1995) *Proc. Natl. Acad. Sci.*, 92:3636–3641).

Accordingly, there exists a need for a model system that can be used to study trinucleotide expansions and their association with chromosome fragility and breakage.

SUMMARY OF THE INVENTION

An object of the present invention is to provide assays to measure the rate of breakage or fragility of a selected trinucleotide repeat by inserting the selected trinucleotide repeat between homologous sequences of *Saccharomyces cerevisiae* and measuring the recombination rate of the homologous sequences. In one embodiment, the insertion of the trinucleotide repeat is between homologous sequences of chromosome II of *Saccharomyces cerevisiae*. In another embodiment, yeast artificial chromosomes (YACs) in *Saccharomyces cerevisiae* are used.

Another object of the present invention is to provide an assay to measure trinucleotide repeat expansion. Because increased fragility is only associated with a long CTC repeat sequence in the above described assay, an increase in tract length can be measured by an increase in breakage. In this embodiment, a short trinucleotide repeat sequence is used initially to look for conditions which increase breakage. A separate assay is then performed to determine whether that condition is able to increase tract length (i.e., cause trinucleotide repeat expansion).

Another object of the present invention is to provide a method of screening for drugs that increase or decrease chromosome breakage specifically at trinucleotide repeats, or increase trinucleotide repeat expansion thus increasing breakage.

Yet another object of the present invention is to provide a method of identifying intracellular conditions or proteins whose mutation or overexpression may increase or decrease chromosome breakage specifically at trinucleotide repeats, or increase trinucleotide repeat expansion thus increasing breakage.

DETAILED DESCRIPTION OF THE INVENTION

The fidelity of DNA replication and the reliable transmission of genetic information from mother cell to daughter cell is one of the hallmarks of the cell. However, in higher organisms such as humans, there exist regions of polymorphism with multiple alleles, which are not always as reliably replicated as Mendelian traits. These regions, characterized by STRs such as trinucleotide repeats, have the potential for genome instability, seen most often as repeat expansions propagated through meiotic and mitotic cell divisions.

A double strand break between two homologous sequences has been demonstrated to increase the recombination between such sequences in *Saccharomyces cerevisiae* by utilizing repair processes (Sugawara and Haber (1992) *Mol. and Cell. Biol.*, 12:563–575). In the assay described by Sugawara and Haber, double stranded breaks were created using the HO endonuclease activity of the yeast cell. The HO cut site was genetically integrated into the chromosome between repeated URA3 sequences. The HO endonuclease was placed under the control of an inducible promoter. When HO was induced, the cut site was cleaved and the two repeated sequences recombined to form one copy of URA3. The double strand break induced recombination between chromosomal repeats was linearly dependent on the length of homology and appeared to have a minimum homology requirement. It was also proposed that a minimum length unit possesses a fixed recombination frequency.

It has now been found that the yeast, *Saccharomyces cerevisiae*, also provides a model system in which to assay phenomenon such as trinucleotide repeat expansion. Based on the association of long trinucleotide repeats with fragile sites on human chromosomes, an assay has now been developed in which a trinucleotide repeat, if prone to breakage and if placed between two homologous sequences, increases recombination between those sequences.

Figure 1:
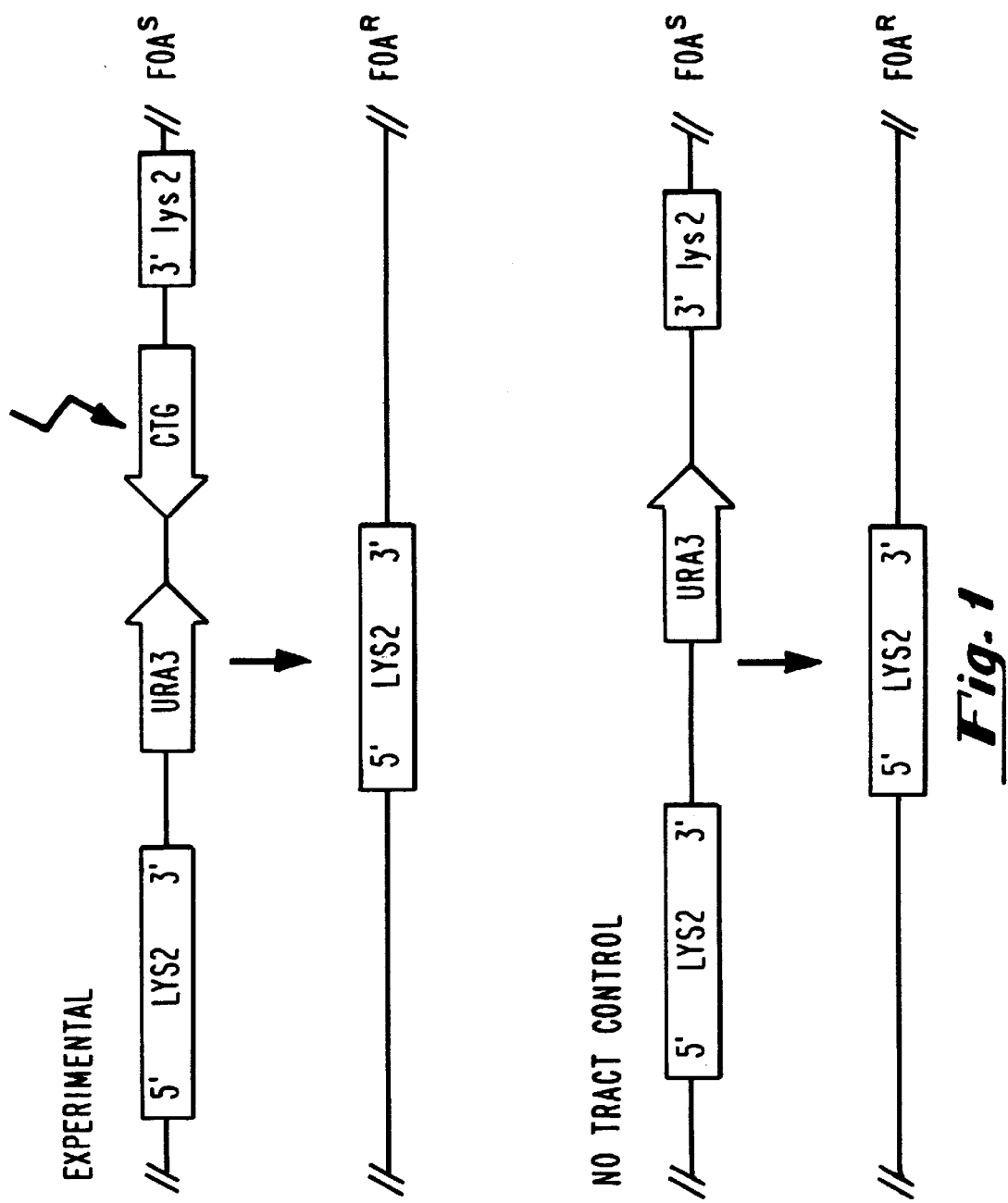
FIG. 1 provides a schematic of the assay for chromosome fragility on chromosome II.

In one embodiment of the invention, a trinucleotide repeat tract and neighboring URA3 gene are placed at the LYS2 locus of *Saccharomyces cerevisiae* chromosome II, flanked by a full length LYS2 gene on one side and a portion of the 3' end of the LYS2 gene on the other side (FIG. 1). Since it contains a functional URA3 gene, this strain is sensitive to the drug 5-fluoro-orotic acid (FOA$^s$). However, if recombination occurs between the flanking homologous LYS2 sequences, both the URA3 gene and the trinucleotide repeat tract are eliminated and the yeast acquires resistance to 5-fluoro-orotic acid (FOA$^r$). Frequency of the recombination event is scored by plating yeast cells on growth medium containing FOA and counting the number of FOA$^r$ cells compared to the number of cells plated. The rate of generation of FOA$^r$ is dependent on the length of the trinucleotide repeat tract. See FIG. 3. For example, a yeast strain containing a (CTG)$^{130}$ tract generates FOAr cells at a rate approximately 10-fold higher, and a (CTG)$^{250}$ tract at a rate approximately 100-fold higher than a yeast strain with no tract control. Thus, this assay serves as a measure of trinucleotide repeat expansion. Only trinucleotide tracts expanded to a length of about 130 repeats or larger will show a positive phenotype.

Figure 2:
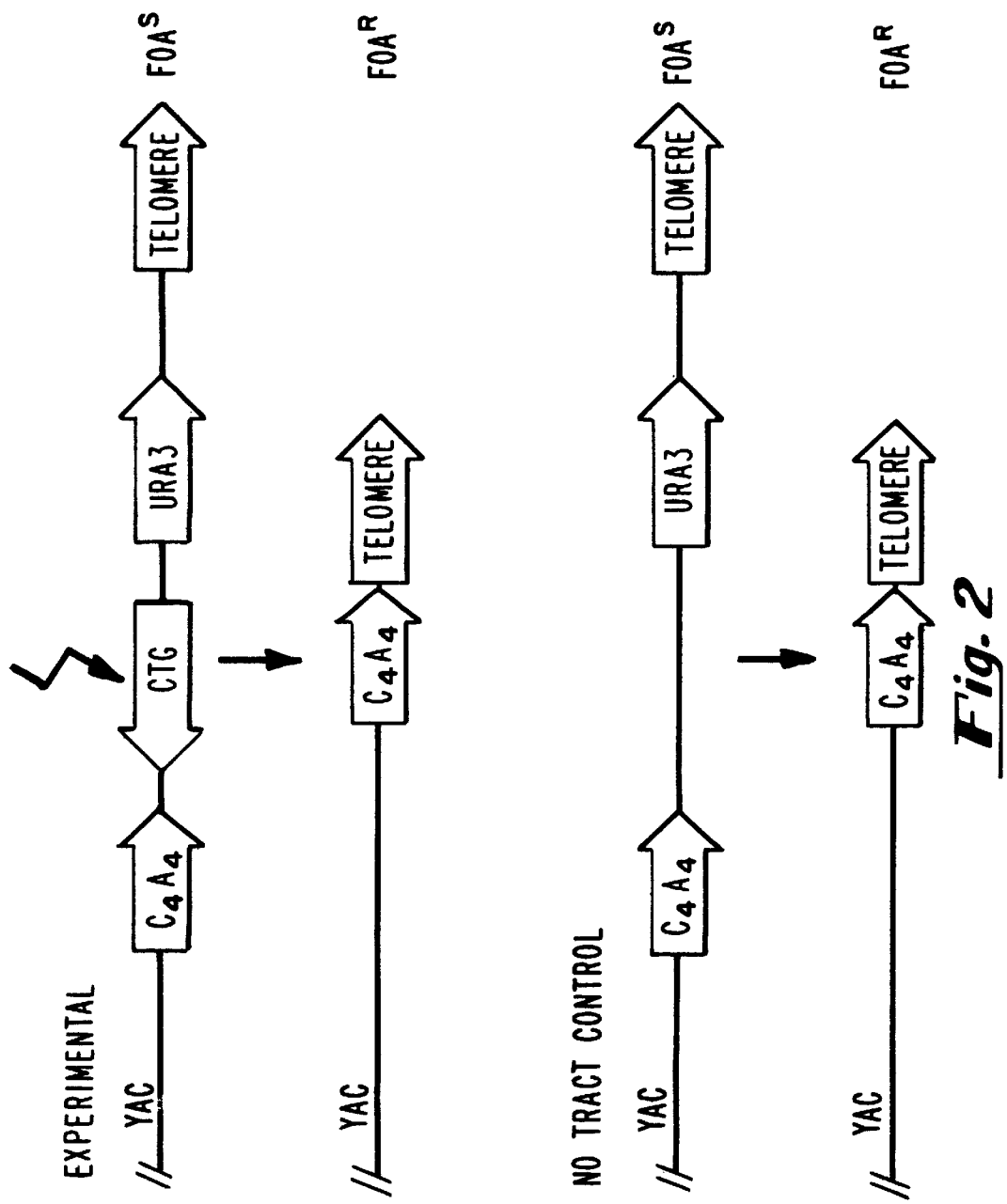
FIG. 2 provides a schematic for chromosome fragility using YAC-CF1.

In another embodiment, expansion of trinucleotide repeats and their ability to act as fragile sites, and thus areas of breakage, are measured using a yeast artificial chromosome (YAC). In this embodiment, a trinucleotide repeat sequence is engineered between the $C_4A_4$ sequence and the URA3 gene in YAC-VS5 (modified from Schulz and Zakian (1994) *Cell*, 76:145–155) to create YAC CF-1 (FIG. 2). Similar to the previous assay, loss of URA3, due breakage at the CTG tract, results in loss of the URA3 gene so that yeast cells harboring this YAC construct become FOA$^r$ This YAC construct is also marked with LEU2, thus a selection for LEU$^+$FOA$^r$ cells yields cells that have retained the YAC but lost a functional URA3 gene. Additionally, the $C^4A^4$ sequence acts as a seed for addition of yeast telomeres, so that the broken chromosome are stabilized by the addition of a new telomere and thus recovered. The background rate of LEU$^+$FOA$^r$ cells either due to breakage or mutation of the URA3 gene is low, approximately 1×10$^6$ colonies per cell per generation (Schulz and Zakian (1994) *Cell*, 76:145–155). Thus, this assay is very sensitive.

Chromosomes of individuals harboring expanded trinucleotide repeat tracts are prone to breakage in vivo, leading to a disease phenotype (Jones et al. (1994) *Hum. Mol. Genet.*, 3:2123–2130; Ashley and Warren (1995) *Ann. Rev. Genet.*, 29:703–728). The assays of the present invention are useful in screening of potential drugs which increase or decrease chromosome breakage specifically at trinucleotide repeats. Cultures used in the assays of the present invention can be contacted with a drug suspected of increasing or decreasing chromosome breakage specifically at trinucleotide repeats prior to measuring a rate of FOA-resistance. The measured rate in cultures with the drug are then compared with a rate measured in cultures without the drug to determine whether the drug increases or decreases the rate of FOA-resistance which is indicative of chromosome breakage.

Similarly, proteins or even cellular conditions that may alter trinucleotide repeat expansion or contraction can also be examined using these assays. Individuals with slightly expanded alleles often pass much larger, disease-causing alleles to their offspring. In addition, expanded trinucleotide repeat tracts can be mitotically unstable, so that they expand in some cells during an individual's lifetime. It is possible that these somatic expansions contribute to worsening of the disease. Further, it is believed that certain conditions including expression of particular proteins may trigger this expansion. Accordingly, using the assays of the present invention, selected cellular conditions can be simulated or proteins can be mutated or overexpressed to determine whether they affect trinucleotide repeat expansion. Because the assay eliminates the repeat, once a condition or protein which consistently increases the rate of FOA-resistance in the assay is identified, the condition is reproduced or the protein is added to yeast cells before they undergo the breakage event. For example, the yeast cells can be plated on media lacking uracil so that only the cells with an intact URA3 gene will grow. Tract length is then measured directly by PCR, Southern blot, or in situ hybridization.

Figure 3:
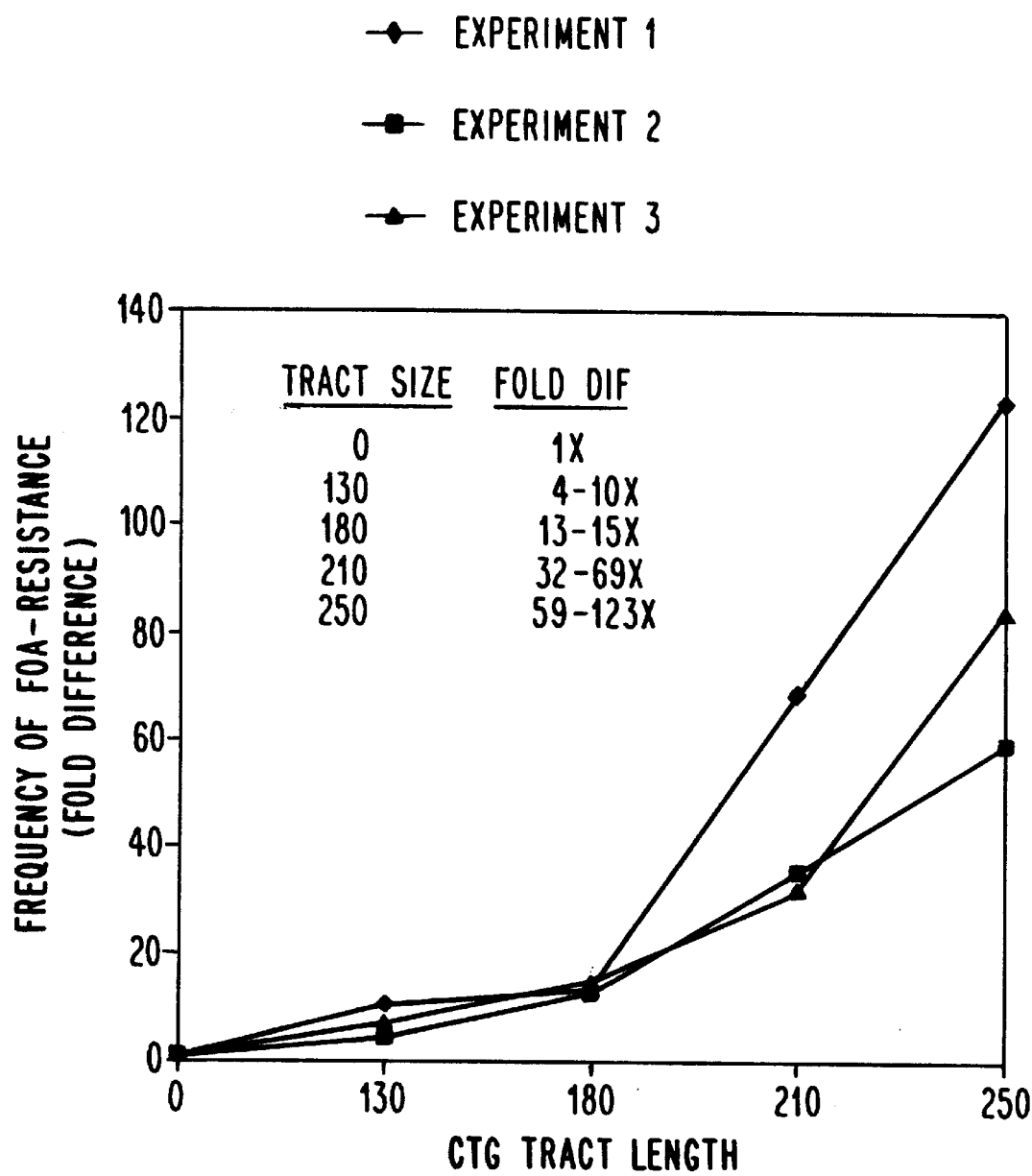
FIG. 3 provides a linegraph showing the frequency of FOA resistance in yeast cells as a function of CTG tract length in three separate experiments.

The YAC system of the present invention can also be modified by incorporating different size trinucleotide repeat tracts into the YAC which can be readily transformed into different yeast backgrounds. As shown in FIG. 3, the CTG-50 tract presently contained in the YAC provides a good starting substrate to screen for increases in breakage or expansion. However, different trinucleotide repeat sequences, for example CCG (rather than CTG), can also be inserted into the chromosome or YAC to test their fragility or expansion. Further, different selectable markers can also be used for the selection. A variety of selectable markers are well known to those skilled in the art.

In both embodiments of the assay of the present invention, a more rapid assay can be performed by streaking or pipetting a small amount of cells from each strain onto an FOA containing plate and visually comparing the number of FOA$^r$ colonies arising.

The following nonlimiting examples are provided to further illustrate the present invention.

EXAMPLES

Example 1

Construction of a chromosome fragility site on chromosome II of *Saccharomyces cerevisiae*

CTG tracts of varying lengths and a neighboring URA3 gene were inserted at the LYS2 locus of chromosome II of *Saccharomyces cerevisiae*, flanked by a full LYS2 gene on one side and approximately 600 bp of the 3' end of the LYS2 gene on the other side. To create the direct repeat recombination strain, strain YPH500L-Ib6 which contains the URA3 gene and CTG-130 tract at the LYS2 locus was transformed with plasmid pSK1 linearized at the EcoRI and PvuII sites. Plasmid pSK1 was made by ligating the URA3 gene on a NruI/PvuII fragment from plasmid YIP5 into the PvuII site of plasmid pTD27 which is at the 5' end of the LYS2 gene contained on pTD27. Cells which had undergone recombination between pSK1 and the 5' LYS2 fragment and URA3 gene at the LYS2 locus of YPHS500L-Ib6, which would convert the 5' LYS2 fragment to a full LYS2 gene, were selected for by plating on YC-LYS media. Because the CTG tract is unstable, transformations with various lengths of CTG tracts were obtained.

Example 2

Construction of a yeast artificial chromosome (YAC) containing a chromosome fragility site YAC-VS5 was modified by placement of CTG tracts of varying length between the $C_4A_4$ sequence and the URA3 gene yielding YAC-CF1. To create YAC-CF1, a CTG tract on a PvuII fragment from plasmid pGEMCTG130 (Wang et al., (1994) *Science*, 265:669) was cloned into the NsiI site of plasmid pVS20 (Schulz and Zakian, (1994) *Cell*, 76:145) to create plasmid pCFN-2. Plasmid pCFN-2 was linearized with AatII, and transformed into yeast strain VPS105 containing YAC-VS5 (transforments selected on YC-URA-LEU plates) to create strain VPS105-YAC-CF1.

Example 3

Increased recombination frequency is correlated with an expansion of CTG tract size Yeast strains harboring various CTG tract sizes in chromosome II were plated on SC-Lys plates. A representative sample (approximately ten colonies) of each strain were cored out of the agar and separately dispersed in water. An aliquot of each was plated on FOA containing media. Another aliquot was plated onto SC-Lys for a viable cell count. In some cases this aliquot was a mixture of all colonies from each strain. The number of FOA-resistant colonies grown after incubation for five days at 30° C. was determined. The recombination frequency is determined by dividing the median number by the number of cells plated. The recombination rate is determined by growing the cells in SC-Lys liquid media and removing aliquots at various time points to plate on FOA-containing media and SC-Lys for a viable cell count as described above.

What is claimed is:

1. An assay for measuring the rate of breakage or fragility of a selected trinucleotide repeat comprising inserting a selected trinucleotide repeat between two homologous sequences on a chromosome in a yeast cell culture and measuring a rate of recombination of the homologous sequences.

2. The assay of claim 1 further comprising the step of exposing the yeast cell culture to a drug, protein or cellular condition suspected of increasing or decreasing chromosome breakage at trinucleotide repeats prior to measuring the rate of recombination and comparing the measured rate to a rate of recombination measured in cultures with no exposure to the drug, protein or cellular condition to determine whether the drug, protein or cellular condition increases or decreases chromosome breakage.

3. An assay for measuring the rate of breakage or fragility of a selected trinucleotide repeat comprising inserting a selected trinucleotide repeat between a URA3 gene and a C4A4 backup telomere sequence of a yeast artificial chromosome in a yeast cell culture and measuring a rate of loss of the URA3 gene.

4. The assay of claim 3 further comprising the step of exposing the yeast cell culture to a drug, protein or cellular condition suspected of increasing or decreasing chromosome breakage at trinucleotide repeats prior to measuring the rate of loss of the URA3 gene and comparing the measured rate of loss to a rate measured in cultures not exposed to the drug, protein or cellular condition to determine whether the drug, protein or cellular condition increases or decreases chromosome breakage.

* * * * *

UNITED STATES PATENT AND TRADEMARK OFFICE
CERTIFICATE OF CORRECTION

PATENT NO. : 5,843,671
DATED : December 1, 1998
INVENTOR(S) : Zakian, et al.

It is certified that error appears in the above-indentified patent and that said Letters Patent is hereby corrected as shown below:

At col 6, line 49, please delete "YPHS500L" and insert therefor --YPH500L--.

Signed and Sealed this

Eighteenth Day of May, 1999

Attest:

Q. TODD DICKINSON

*Attesting Officer*   Acting Commissioner of Patents and Trademarks